US006982340B2

(12) United States Patent
Mumura et al.

(10) Patent No.: US 6,982,340 B2
(45) Date of Patent: Jan. 3, 2006

(54) PROCESS FOR PRODUCING AN ESTER

(75) Inventors: Taku Mumura, Wakayama (JP); Hidetoshi Kadowaki, Wakayama (JP); Futoshi Nishigaki, Wakayama (JP)

(73) Assignee: Kao Corporation, Tokyo (JP)

( * ) Notice: Subject to any disclaimer, the term of this patent is extended or adjusted under 35 U.S.C. 154(b) by 8 days.

(21) Appl. No.: 10/384,596

(22) Filed: Mar. 11, 2003

(65) Prior Publication Data
US 2003/0225304 A1  Dec. 4, 2003

(30) Foreign Application Priority Data
Mar. 13, 2002  (JP) ............................... 2002-68961

(51) Int. Cl.
C07C 51/36  (2006.01)
C07C 67/02  (2006.01)
C07C 27/04  (2006.01)

(52) U.S. Cl. ...................... 554/142; 554/191; 560/261; 568/885

(58) Field of Classification Search ............... 560/261; 568/885; 554/142, 174, 191
See application file for complete search history.

(56) References Cited

U.S. PATENT DOCUMENTS

| 2,396,646 | A | * | 3/1946 | Dressler ................... 260/97.5 |
| 2,721,872 | A | * | 10/1955 | Mattikow et al. ......... 260/412.5 |
| 5,120,885 | A | * | 6/1992 | Tsukada et al. ............. 568/885 |
| 5,525,126 | A | * | 6/1996 | Basu et al. .................. 44/308 |
| 2002/0115875 | A1 | * | 8/2002 | Kaimal et al. .............. 554/174 |

FOREIGN PATENT DOCUMENTS

| JP | 56-71037 | * | 6/1981 |
| JP | 6-033086 | | 2/1994 |
| JP | 2544552 | | 7/1996 |
| JP | 2934073 | | 5/1999 |

OTHER PUBLICATIONS

Hartman, L., "Direct Conversion of Soaps into Methyl Esters" J. Am. Oil Chemists' Society, vol. 34, p. 165 (1957)—as Abstracted by Caplus.*
The Merck Index, 13th ed. ©2001 by Merck & Co., Inc., p. 1222.*
Schmidt et al, "Purification of Palm Oil" Maslozhirovaya Promyshiennost, vol. 10 pp. 18-21 (1978) with English Translation.*
Kirk-Othmer Encyclopedia of Chemical Technology, 4th ed. vol. 5, pp. 346-348 "Catalyst Components" ©1993 by John Wiley & Sons, Inc.*

* cited by examiner

Primary Examiner—James O. Wilson
Assistant Examiner—Zachary C. Tucker
(74) Attorney, Agent, or Firm—Oblon, Spivak, McClelland, Maier & Neustadt, P.C.

(57) ABSTRACT

There is provided a process wherein a lower alkyl ester of a fatty acid derived from natural fats and oils and a lower alcohol containing 1 to 4 carbon atoms is produced in a lower sulfur content at lower costs without causing a reduction in yield and a deterioration in selectivity, as well as a process for producing an alcohol without reducing the activity of a catalyst. The process comprises the step of adsorption treatment of an ester with at least one adsorbent selected from clay and activated carbon. Further are provided a process for producing an ester which further comprises adsorption treatment with a hydrogenating decomposition-type adsorbent containing Ni and/or Cu, in hydrogen or a mixed gas atmosphere of hydrogen and an inert gas, and a process for producing an alcohol which comprises hydrogenation reaction with an ester produced by any one of these processes as the starting material.

26 Claims, No Drawings

PROCESS FOR PRODUCING AN ESTER

TECHNICAL FIELD OF THE INVENTION

This invention relates to a process for producing a low-sulfur-content ester of a fatty acid derived from natural fats and oils and a lower alcohol, as well as a process for producing an alcohol from an ester obtained by the above process as the starting material without reducing the activity of a catalyst.

PRIOR ARTS

An ester of a fatty acid derived from natural fats and oils and a lower alcohol containing 1 to 4 carbon atoms usually contains sulfur at a concentration of at least 2 to 10 mg/kg. In the case where such an ester is subjected to hydrogenation reaction in the presence of a hydrogenation catalyst to produce an alcohol, the content of sulfur contained in the ester acts as a catalyst poison on the hydrogenation catalyst, to reduce the activity of the catalyst. Particularly, in the case of fixed-bed continuous reaction, the life of the catalyst is made very short, and therefore the catalyst should be frequently exchanged thus inevitably reducing the working efficiency of facilities.

Accordingly, various studies have been conducted for the purpose of removing a sulfur content as a catalyst poison on the hydrogenation catalyst. For example, because sulfur compounds have a relatively high boiling point, a method of reducing a sulfur concentration by distillation is often adopted. However, removal of all sulfur compounds by distillation is not possible, and for reducing the sulfur concentration to a low level of about 0.5 mg/kg, originally required high-boiling components should be disposed off in large amounts, resulting in a significant reduction in the yield.

Desulfurization catalysts based on molybdenum and tungsten, used in the petrochemical field, require high temperatures of 300° C. or more. When esters of fatty acids derived from natural fats and oils are subjected to hydrogenation treatment at such high temperatures, fatty acids and other decomposed products are formed in large amounts as by-products with the progress of the hydrogenating decomposition of ester groups, to cause the problem of deterioration of the ester qualities.

To solve the problems described above, a method of hydrogenating decomposition of sulfur compounds in a hydrogen atmosphere and then adsorbing them onto an adsorbent containing a metal such as Ni and Cu is disclosed in e.g. Japanese Patent Nos. 2544552 and 2934073. For maintaining intended adsorption performance, however, the expensive adsorbent should be frequently exchanged or large-scale adsorption facilities should be installed, resulting in the problem of higher costs in adsorption treatment.

JP-A 6-33086 shows desulfurization conducted by fats and oils and silica gel.

DISCLOSURE OF INVENTION

The object of this invention is to provide a process for producing a low-sulfur-content ester of a fatty acid derived from natural fats and oils and a lower alcohol containing 1 to 4 carbon atoms without causing a deterioration in selectivity and a reduction in yield due to formation of by-products etc., as well as a process for producing an alcohol from an ester obtained by the above process as the starting material without reducing the activity of a catalyst.

The inveniton provides a process for preparing an ester compound, which comprises reacting a fatty acid derived from natural fats and oils with an alcohol having 1 to 4 carbon atoms and then adsorption-treating the obtained ester compound with at least one adsorbent (Adsorbent A) selected from the group consisting of clay and activated carbon.

In other words the invention provides a process for purifying an ester compound, which comprises adsorption-treating the ester compound obtainable by reacting a fatty acid derived from natural fats and oils with an alcohol having 1 to 4 carbon atoms with at least one adsorbent (Adsorbent A) selected from the group consisting of clay and activated carbon.

The processes shown above may further comprise adsorption-treating the product with a hydrogenating decomposition-type adsorbent comprising Ni and/or Cu (hereinafter, referred to as adsorbent "B") in hydrogen gas or a mixed gas of hydrogen gas and an inert gas.

The invention then provides a process for preparing an alcohol, which comprises hydrogenating the ester compound obtained by the process defined above.

DETAILED DESCRIPTION OF INVENTION

The production of an ester of a fatty acid derived from natural fats and oils and a lower alcohol containing 1 to 4 carbon atoms is carried out by transesterification between natural fats and oils and a lower alcohol containing 1 to 4 carbon atoms.

The natural fats and oils used herein include animal fats and oils such as tallow and fish oil and vegetable fats and oils such as palm kernel oil, coconut oil, palm oil, soybean oil, and rapeseed oil. In particular, fats and oils having $C_{8-22}$ fatty acids as constituent fatty acids are preferable, and in particular vegetable fats and oils are preferable.

The lower alcohol having 1 to 4 carbon atoms includes methanol, ethanol, 1-propanol, 2-propanol, 1-butanol, etc.

The transesterification can be carried out in any known methods. For the reaction, either a continuous reaction system or a batch system can be utilized, but when the ester is produced in large amounts, the continuous reaction is advantageous. As the transesterification catalyst, a homogenous alkali catalyst such as sodium hydroxide, potassium hydroxide, and sodium alcoholate is generally used, but a solid catalyst such as ion-exchange resin, hydrous zirconium hydroxide, aluminum phosphate, and sulfuric acid-doped zirconia, titanosilicate can also be used. When the homogenous alkali catalyst is used, the reaction is carried out generally under the following conditions. The reaction temperature is 30 to 90° C., preferably 40 to 80° C., and the reaction pressure is in the range of atmospheric pressure to 0.5 MPa, and preferably the reaction is carried at atmospheric pressures. From the viewpoint of costs and reactivity, the lower alcohol containing 1 to 4 carbon atoms is used preferably in an amount of 1.5 to 10 moles per mole of the starting fats and oils. When free fatty acids are contained in the starting fats and oils, it is also effective that before the transesterification with the alkali catalyst, the fatty acids are previously esterified by the use of an acid catalyst such as sulfuric acid, and p-toluenesulfonic acid.

The ester in this invention is suitable as an ester used for production of an alcohol obtained particularly by catalystic reaction.

The thus obtained ester of a fatty acid derived from natural fats and oils and a lower alcohol containing 1 to 4 carbon atoms is subjected to adsorption treatment with the adsorbent "A", whereby an ester with a low sulfur concentration can be produced.

As the adsorbent "A", generally commercially available inexpensive clay or activated carbon can be used, and the clay is preferable. The clay includes, for example, activated clay or acid clay consisting essentially of naturally occurring montmorilonite-based clay, or a purified product of such clay, and synthetic clay, and from the viewpoint of costs and adsorption performance, activated clay and acid clay are preferable.

Depending on the adsorption treatment system and the form of a reaction unit, the shape of the adsorbent "A" can be selected suitably from those of powdery, spherical and cylindrical moldings. As the adsorption treatment system, any of continuous, semi-batch or batch systems can be used, and in the case of continuous treatment, either of a suspension system or a fixed-bed system can be used.

The temperature for adsorption treatment with the adsorbent "A" is preferably 10 to 150° C., more preferably 30 to 130° C., from the viewpoint of suppressing side reactions such as ester decomposition. Generally, in the case of bleaching treatment of fats and oils with activated clay, the treatment is carried out under dehydration conditions such as high temperature, reduced pressure, but in this invention, sulfur adsorption is intended, and thus the dehydration conditions are not necessarily required, and sufficient adsorption is feasible at low temperatures such as room temperature or thereabout. The pressure may be either atmospheric pressure or reduced pressure to achieve the treatment.

The atmospheric gas in the treatment is not limited, and an arbitrary atmospheric gas such as air, an inert gas such as nitrogen or argon, hydrogen gas, or a mixed gas thereof, can be selected. When only treatment with the adsorbent "A" is conducted, air or nitrogen is preferable.

The amount of the adsorbent "A" is preferably 0.01 to 10.0% by weight, more preferably 0.1 to 3.0% by weight, still more preferably 0.2 to 2.0% by weight for use, relative to the ester.

It is known in the prior art to conduct the adsorption treatment (activated clay treatment) of fats and oils, but its effect on removal of sulfur compounds is low. On the other hand, the adsorption treatment, with the adsorbent "A", of the ester of a fatty acid derived from fats and oils and a lower alcohol containing 1 to 4 carbon atoms exhibits a significant effect on removal of sulfur compounds. This is probably because as a solvent for adsorbing sulfur compounds, the ester of lower alcohol is superior to fats and oils and because as compared with sulfur compounds present in fats and oils, sulfur compounds present in the ester of lower alcohol are in such a form to be easily adsorbed.

It is also effective that the ester of lower alcohol before or after adsorption treatment with the adsorbent "A" is subjected, in such a range as not to reduce the yield, to distillation for removal of impurities and for further reduction in the sulfur concentration.

In this invention, an ester of further lower sulfur concentration can be produced by the use of the step adsorption treatment with the adsorbent "B" in hydrogen or a mixed gas atmosphere of hydrogen and an inert gas in combination with the above step of adsorption treatment with the adsorbent "A". With respect to the order of the step of adsorption treatment with the adsorbent "A" and the step of adsorption treatment with the adsorbent "B", any methods of conducting the adsorption treatment with the adsorbent "A" and then the adsorption treatment with the adsorbent "B", or conducting the adsorption treatment with the adsorbent "B" and then the adsorption treatment with the adsorbent "A", or conducting these adsorption treatments simultaneously are effective for carrying out this invention, but the method of conducting the adsorption treatment with the adsorbent "A" and then the adsorption treatment with the adsorbent "B" is preferable.

The adsorbent "B" used in this invention is a hydrogenating decomposition-type adsorbent containing Ni, and/or Cu, which hydrogenates and decomposes sulfur compounds, to adsorb them as sulfides. Usually, the adsorbent "B" is preferably an adsorbent carried on, or mixed with, carriers, and the Ni content is preferably 10 to 200% by weight based on the carrier component, and the atomic ratio of Cu to Ni (Cu/Ni) is preferably 0 to 8. The carriers used herein are selected from known carriers such as silica, alumina, silica-almina, zeolite, diatomaceous earth, activated clay, titania, zirconia, and activated carbon. The shape of the adsorbent "B" is selected suitably from those of powdery, spherical and cylindrical moldings, depending on the adsorption treatment system.

As the adsorption treatment system with the adsorbent "B", any generally used systems such as suspension system, and fixed-bed system can be used. In the case of large-scale treatment, a continuous fixed-bed system is advantageous.

When the adsorption treatment is conducted continuously in the fixed-bed system, the treatment is carried out under the following conditions. The atmospheric gas is preferably hydrogen or a mixed gas of an inert gas containing 1% by volume or more of hydrogen, and the inert gas includes nitrogen, argon, helium and methane. The flow rate of hydrogen or a hydrogen-mixed gas is determined preferably in such a range that the molar ratio of hydrogen to the ester group whose molar ratio is calculated from the saponification value of the ester treated is 0.1 to 300. The pressure of the atmospheric gas is preferably 0.01 to 50 MPa, more preferably 0.1 to 30 MPa. From the viewpoint of achieving a sufficient adsorption rate, the treatment temperature is preferably 40° C. or more, more preferably 50° C. or more. From the viewpoint of suppressing side reactions such as hydrogenating decomposition, the treatment temperature is preferably 250° C. or less, more preferably 200° C. or less. The liquid hourly space velocity (LHSV) of the ester is preferably 0.1 or more from the viewpoint of improving productivity and suppressing side reactions such as hydrogenating decomposition, and simultaneously the LHSV is preferably 5 or less from the viewpoint of achieving sufficient adsorption performance.

In the case where the ester treated with the adsorbent "A" is subjected subsequently to adsorption treatment with the adsorbent "B", the rate of adsorption thereof onto the adsorbent "B" is significantly improved as compared with the rate of adsorption in the case where the ester not treated with the adsorbent "A" is subjected to adsorption treatment with the adsorbent "B". This effect on improvement of the adsorption rate means that sulfur compounds hardly adsorbed onto the adsorbent "B" are adsorbed selectively (or preferentially) in the step of adsorption treatment with the adsorbent "A". That is, the particularly outstanding effect of this invention is attributable to the selectivity of sulfur compounds to be adsorbed in the respective steps, that is, the step of adsorption treatment with the adsorbent "A" and the step of adsorption treatment with the adsorbent "B", and by combining the respective steps, an ester of further lower sulfur content can be produced.

A further advantage achieved by combining the steps of adsorption treatments with the adsorbents A and B lies in that the adsorption loading of the expensive adsorbent "B" can be significantly reduced. For example, when the adsorbent "B" is used in the suspension system, the amount of the adsorbent used can be reduced, the treatment time can be shortened, and the treatment conditions can be made moderate. On one hand, when it is used in the fixed-bed system, the amount of the adsorbent used can be reduced, and the life of the adsorbent "B" can be significantly improved. In this case, the adsorption performance of the adsorbent "B" can be demonstrated to the maximum degree in small-scale facilities for a prolonged period of time without the necessity for frequent exchange of the expensive adsorbent "B", bringing about a significant reduction in costs.

The ester of lower sulfur content produced by the process of this invention is particularly useful as a starting material for producing an alcohol by hydrogenation reaction in the presence of a hydrogenation catalyst. Because of the lower sulfur content, there is less drop in the activity of the hydrogenation catalyst, and particularly in the fixed-bed continuous reaction, the life of the catalyst can be significantly improved.

Hereinafter, the process for producing an alcohol by hydrogenating the ester of lower sulfur content produced in this invention will be described.

As the hydrogenation catalyst, generally known catalysts based on copper or on noble metals such as palladium and platinum are used. The copper-based catalysts include copper-chrome, copper-zinc, copper-iron-aluminum, and copper-silica. In the presence of any of the catalysts described above, the hydrogenation reaction can be carried out in any of generally used reaction systems such as liquid-phase suspension bed system, and fixed-bed system.

When the reaction is carried out in the liquid-phase suspension bed system, the amount of the catalyst though being preferably 0.1 to 20% by weight based on the ester can be selected arbitrarily in such a range as to achieve a practical reaction yield, depending on the reaction temperature or reaction pressure. The reaction temperature is preferably 160 to 350° C., more preferably 200 to 280° C. The reaction pressure is preferably 0.1 to 35 MPa, preferably 3 to 30 MPa.

When the reaction is carried out continuously in the fixed-bad system, the catalyst molded in a cylindrical, pellet or spherical form is used. The reaction temperature is preferably 130 to 300° C., more preferably 150 to 270° C., and the reaction pressure is preferably 0.1 to 30 MPa. In consideration of productivity and reactivity, LHSV is determined arbitrarily depending on the reaction conditions.

According to this invention, a lower alkyl ester of a fatty acid derived from natural fats and oils can be produced in a lower sulfur content at lower costs without causing a deterioration in selectivity and a reduction in yield due to formation of by-products. Further, an alcohol can be produced from the ester obtained by the process of the invention as the starting material without lowering the activity of a catalyst.

EXAMPLE

The measurement of sulfur concentrations in the Examples was carried out using Trace Level Total Sulfur Content Analyzer 7000 TS manufactured by ANTEK Co., Ltd.

Example 1

24 weight-% methanol, 0.10 weight-% of 98% sulfuric acid were added to palm kernel oil treated previously with activated clay (0.5% WAC REGULAR 1B (trade name), manufactured by TAIKO CLAY MARKETING SDN. BHD, 115° C., 15 kPa), and the mixture was reacted at 70° C. for 1 hour. Subsequently, the glycerin layer formed was removed, while 0.30 weight-% caustic soda and 10 weight-% methanol were added in 3 divided portions to the palm kernel oil and reacted at 50° C. for 3 hours. After the reaction, the oil layer was washed with water to give a palm kernel oil fatty methyl ester. The resulting palm kernel oil fatty methyl ester was further distilled to give a palm kernel oil fatty methyl ester having a sulfur concentration of 0.75 mg/kg.

The above methyl ester, 50 g, and activated clay manufactured by Mizusawa Kagaku Kogyo Co., Ltd. (trade name: Gareon Earth NS), 0.5 g (1.0 weight-% based on the methyl ester) were introduced into a 100-ml flask and stirred at 60° C. for 90 minutes at atmospheric pressures. The activated clay was removed by a filtration procedure, and the concentration of sulfur in the methyl ester was measured, and the reduction in the amount of sulfur and the degree of adsorption were determined from the following formulas. The results are shown in Table 1.

Reduction in the amount of sulfur [mg/kg]=$S_0 - S_1$

Degree of adsorption (%)=$(S_0 - S_1) \times 100 / S_0$

In the formulas, $S_0$ represents the concentration of sulfur [mg/kg] before adsorption treatment with the adsorbent "A", and $S_1$ represents the concentration of sulfur [mg/kg] after adsorption treatment with the adsorbent "A".

Example 2

The adsorption treatment was conducted in the same manner as in Example 1 except that the amount of the activated clay (Gareon Earth NS) used was 0.5 weight-% based on the methyl ester, and the reduction in the amount of sulfur and the degree of adsorption were determined in the same manner. The results are shown in Table 1.

Example 3

The adsorption treatment was conducted in the same manner as in Example 1 except that the amount of the activated clay (Gareon Earth NS) used was 3.0 weight-% based on the methyl ester and the treatment time was set to 180 minutes, and the reduction in the amount of sulfur and the degree of adsorption were determined in the same manner. The results are shown in Table 1.

Example 4

The adsorption treatment was conducted in the same manner as in Example 1 except that activated carbon (trade name: YP-17) manufactured by Kuraray Chemical Co., Ltd. was used in an amount of 1.0 weight-% based on the methyl ester, and the reduction in the amount of sulfur and the degree of adsorption were determined in the same manner. The results are shown in Table 1.

Comparative Example 1

The adsorption treatment was conducted in the same manner as in Example 1 except that silica-alumina (trade name: KW#700) manufactured by Kyowa Chemical Industry Co., Ltd., consisting of silica and alumina, similar to activated clay, was used in an amount of 1.0 weight-% based on the methyl ester, and the reduction in the amount of sulfur and the degree of adsorption were determined in the same manner. The results are shown in Table 1.

TABLE 1

| | Adsorbent | Amount of adsorbent (weight-% based on ester) | Treatment time (minutes) | Reduction in amount of sulfur [mg/kg] | Degree of adsorption [%] |
|---|---|---|---|---|---|
| Example 1 | Activated clay (Gareon Earth NS) | 1.0 | 90 | 0.28 | 37 |
| Example 2 | Activated clay (Gareon Earth NS) | 0.5 | 90 | 0.22 | 29 |
| Example 3 | Activated clay (Gareon Earth NS) | 3.0 | 180 | 0.39 | 52 |
| Example 4 | Activated carbon (YP-17) | 1.0 | 90 | 0.15 | 20 |
| Comparative Example 1 | Silica-alumina (KW#700) | 1.0 | 90 | 0.02 | 3 |

As is evident from Table 1, the sulfur concentration was significantly reduced in the Examples in this invention in spite of the previous treatment of fats and oils with activated clay.

Example 5

The methyl ester was subjected to adsorption treatment with the adsorbent "A" under the same conditions as in Example 1 except that the amount of the methyl ester was 300 g, the amount of activated clay (trade name: Gareon Earth NS) used was 3.0 g (1.0 weight-% based on the methyl ester), and the treatment time was 180 minutes, and the thus treated methyl ester (sulfur concentration 0.42 mg/kg) was subjected to the following adsorption treatment with the adsorbent "B".

As the adsorbent "B", Ni/silica-alumina (trade name: C46-7 RS; composition: Ni=52%, silica-alumina carriers 38%; a extrusion-molded product with a diameter 1/16 inch, manufactured by SÜD-CHEMIE Inc.), 2.0 g (1.0 weight-% based on the methyl ester), was introduced into a basket which was then attached to a stirring blade in a 500-mL autoclave. 200 g of the above methyl ester treated with the adsorbent "A" was introduced into the autoclave, the atmosphere in the autoclave was replaced by hydrogen, and then the methyl ester was heated to 135° C. under hydrogen flow at 10 L/min. After temperature reached 135° C., hydrogen was introduced to increase the pressure to 24.5 MPa, and at this stage, the adsorption treatment time was regarded as 0. Sampling was conducted during the treatment, and the adsorption treatment was conducted for 120 minutes in total. From the sulfur concentrations in samples, the adsorption rate was determined according to the following formula. The results are shown in Table 2.

Adsorption rate=$\ln(S_0/S_t)/t$ wherein $S_0$ is the concentration of sulfur [mg/kg] in 0 hour, and $S_t$ is the concentration of sulfur [mg/kg] in t hours.

Comparative Example 2

200 g of the methyl ester (sulfur concentration 0.75 mg/kg) not subjected to adsorption treatment with the adsorbent "A", used in Example 1, was subjected to adsorption treatment with the adsorbent "B" under the same conditions as in Example 5, and the adsorption rate was determined in the same manner. The results are shown in Table 2.

TABLE 2

| | Methyl ester before adsorption treatment with adsorbent "B" | Sulfur concentration [mg/kg] | | Adsorption rate [h$^{-1}$] |
|---|---|---|---|---|
| Example 5 | Treated with activated clay Sulfur concentration 0.42 mg/kg | in 0 hour 0.30 | in 1 hour 0.01 | 3.4 |
| Comparative Example 2 | Not treated with adsorbent "A" Sulfur concentration 0.75 mg/kg | in 0 hour 0.74 | in 2 hours 0.05 | 1.3 |

Example 6

24 Weight-% methanol and 0.10 weight-% of 98% sulfuric acid were added to crude coconut oil and reacted at 70° C. for 1 hour. Subsequently, the formed glycerin layer was removed, while 0.25 weight-% caustic soda and 9 weight-% methanol were added in 3 divided portions to the coconut oil and reacted at 50° C. for 4 hours. After the reaction, the oil layer was washed with water to give a coconut oil fatty methyl ester having a sulfur concentration of 2.8 mg/kg.

The resulting coconut oil fatty methyl ester, 2000 g, was introduced into a 3-L flask, and activated clay (trade name: PAGODA, P. T. MADU LINGGA PERKASA Co., Ltd.), 10 g (0.5 weight-% based on the methyl ester), was added thereto as adsorbent "A" and stirred at 60° C. for 1 hour at atmospheric pressures. The concentration of sulfur in the methyl ester in a filtrate obtained by filtration was 2.1 mg/kg.

The above methyl ester, 1700 g, treated with the adsorbent "A" was distilled (bottom-cut). The distillation conditions were as follows: Sulzer packing (number of theoretical stages=5) was used; reflux ratio=1; the final bottom temperature, 240° C.; the column top pressure, 0.8 kPa, and the distillation yield, 97%. The concentration of sulfur in the methyl ester after distillation was 0.53 mg/kg.

Subsequently, the adsorption treatment with the adsorbent "B" was carried out in the same manner as in Example 5 except that this bottom-cut methyl ester was used, and the rate of adsorption was determined. The results are shown in Table 3.

Comparative Example 3

A coconut oil fatty methyl ester (sulfur concentration 2.8 mg/kg) obtained by transesterification of crude coconut oil with methanol in the same manner as in Example 6 was subjected, without adsorption treatment with the adsorbent "A", to distillation (bottom cutting) under the same conditions. The concentration of sulfur in the methyl ester after distillation was 0.78 mg/kg.

Subsequently, adsorption treatment with the adsorbent "B" was carried out in the same manner as in Example 5 except that this bottom-cut methyl ester was used, and the rate of adsorption was determined. The results are shown in Table 3.

TABLE 3

| | Methyl ester before adsorption treatment with adsorbent "B" | Sulfur concentration [mg/kg] | | Adsorption rate [h$^{-1}$] |
|---|---|---|---|---|
| Example 6 | Distilled after treatment with activated clay Sulfur concentration 0.53 mg/kg | in 0 hour 0.32 | in 1 hour 0.01 | 3.5 |
| Comparative Example 3 | Distilled, untreated methyl ester Sulfur concentration 0.78 mg/kg | in 0 hour 0.44 | in 1 hour 0.01 | 2.4 |

Example 7

A coconut oil fatty methyl ester obtained by transesterification of crude coconut oil with methanol in the same manner as in Example 6 was subjected to adsorption treatment with activated clay (the same adsorbent "A" as in Example 6) in an amount of 0.5 weight-% based on the methyl ester, under the conditions of 60° C., atmospheric pressures and 1 hour. After filtration, distillation was performed to give a methyl ester fraction having a sulfur concentration of 1.4 mg/kg.

This methyl ester fraction was subjected to adsorption treatment with the adsorbent "B" and hydrogenation reaction successively in a fixed-bed reaction unit, under the following conditions: The fixed-bed reaction unit was equipped with two columns in series wherein the first column was charged with 200 mL Ni/silica-alumina (the same adsorbent "B" as in Example 5) and the second column was charged with 400 mL copper-zinc catalyst carried on titania (composition: Cu=35%, Zn=1.8%; 50% TiO$_2$ carriers; shape: 3.2 mmφ×3.2 mm cylindrical shape) The conditions for adsorption onto the first column charged with the adsorbent "B" were that the pressure was 19.6 MPa, the temperature was 90° C., and the feed rate of the methyl ester was 400 mL/h. The concentration of sulfur in the methyl ester after treatment with the first column was 0.25 mg/kg.

The conditions for hydrogenation reaction in the second column charged with the hydrogenation catalyst were that the pressure was 19.6 MPa, and the temperature was 220° C.

The GC yield of an alcohol obtained after the hydrogenation reaction was 93.7%, and the saponification value was 15.2 mg KOH/g.

What is claimed is:

1. A process for purifying an ester compound, which comprises preparing an ester compound and then adsorption-treating the obtained ester compound with
    at least one adsorbent (Adsorbent A) selected from the group consisting of clay and activated carbon, and
    a hydrogenating decomposition-type adsorbent comprising Ni and/or Cu (hereinafter, referred to as adsorbent "B") in hydrogen gas or a mixed gas of hydrogen gas and an inert gas,
    wherein said preparing comprises either:
    (a) transesterification of natural fats and oils with a lower alcohol having 1 to 4 carbon atoms, or
    (b) esterification of a fatty acid derived from natural fats and oils with a lower alcohol having 1 to 4 carbon atoms.

2. The process according to claim 1, wherein the adsorbent "A" is clay.

3. The process according to claim 1, wherein the adsorbent "A" is activated clay.

4. The process according to claim 1, wherein the adsorption treatment with the adsorbent "A" is performed at 10 to 150° C.

5. The process according to claim 1, wherein after the adsorption treatment with the adsorbent "A", the adsorption treatment with the adsorbent "B" is performed.

6. A process for preparing an alcohol, which comprises further hydrogenating the ester compound obtained by the process defined in claim 1.

7. The process according to claim 1, wherein said preparing comprises transesterification of natural fats and oils with a lower alcohol having 1 to 4 carbon atoms.

8. The process according to claim 7, wherein said natural fats and oils are selected from the group consisting of tallow oil, fish oil, palm kernel oil, coconut oil, palm oil, soybean oil, and rapeseed oil.

9. The process according to claim 7, wherein said natural fats and oils contain a constituent having $C_{8-22}$ fatty acids.

10. The process according to claim 7, wherein said lower alcohol having 1 to 4 carbon atoms is selected from the group consisting of methanol, ethanol, 1-propanol, 2-propanol, and 1-butanol.

11. The process according to claim 7, wherein said preparing is in the presence of a transesterification catalyst, which is a solid catalyst selected from the group consisting of ion-exchange resin, hydrous zirconium hydroxide, aluminum phosphate, sulfuric acid-doped zirconia, and titanosilicate.

12. The process according to claim 7, wherein said lower alcohol having 1 to 4 carbon atoms is present in an amount ranging from 1.5 to 10 moles per mole of the starting fats and oils.

13. The process according to claim 1, wherein said adsorbent "A" is in a form selected from the group consisting of powdery molding, spherical molding, and cylindrical molding.

14. The process according to claim 1, wherein said adsorption-treating with adsorbent "A" is performed under dehydration conditions.

15. The process according to claim 1, wherein the amount of adsorbent "A" ranges from 0.01 to 10.0% by weight relative to the ester.

16. The process according to claim 1, wherein said adsorbent "B" is in a form selected from the group consisting of powdery molding, spherical molding, and cylindrical molding.

17. The process according to claim 1, wherein said adsorbent "B" is carried on or mixed with a carrier.

18. The process according to claim 17, wherein said carrier is selected from the group consisting of silica, alumina, silica-almina, zeolite, diatomaceous earth, activated clay, titania, zirconia, and activated carbon.

19. The process according to claim 17, wherein the Ni content of said adsorbent "B" ranges from 10 to 200% by weight based on the carrier component.

20. The process according to claim 17, wherein the atomic ratio of Cu to Ni of said adsorbent "B" ranges from 0 to 8.

21. The process according to claim 1, wherein said preparing comprises esterification of a fatty acid derived from natural fats and oils with a lower alcohol having 1 to 4 carbon atoms.

22. The process according to claim 21, wherein said natural fats and oils are selected from the group consisting of tallow oil, fish oil, palm kernel oil, coconut oil, palm oil, soybean oil, and rapeseed oil.

23. The process according to claim 21, wherein said natural fats and oils contain a constituent having $C_{8-22}$ fatty acids.

24. The process according to claim 21, wherein said lower alcohol having 1 to 4 carbon atoms is selected from the group consisting of methanol, ethanol, 1-propanol, 2-propanol, and 1-butanol.

25. The process according to claim 21, wherein said preparing is in the presence of a transesterification catalyst, which is a solid catalyst selected from the group consisting of ion-exchange resin, hydrous zirconium hydroxide, aluminum phosphate, sulfuric acid-doped zirconia, and titanosilicate.

26. The process according to claim 21, wherein said lower alcohol having 1 to 4 carbon atoms is present in an amount ranging from 1.5 to 10 moles per mole of the starting fats and oils.

* * * * *

UNITED STATES PATENT AND TRADEMARK OFFICE
CERTIFICATE OF CORRECTION

PATENT NO. : 6,982,340 B2
DATED : January 3, 2006
INVENTOR(S) : Mimura et al.

It is certified that error appears in the above-identified patent and that said Letters Patent is hereby corrected as shown below:

<u>Title page,</u>
Item [75], should read:
-- [75] Inventors: Taku Mimura, Wakayama (JP);
                   Hidetoshi Kadowaki, Wakayama (JP);
                   Futoshi Nishigaki, Wakayama (JP) --.

Signed and Sealed this

Fourteenth Day of March, 2006

JON W. DUDAS
*Director of the United States Patent and Trademark Office*